(12) United States Patent
Delano et al.

(10) Patent No.: US 9,259,553 B2
(45) Date of Patent: Feb. 16, 2016

(54) STYLET HANDLE ATTACHMENT DEVICE

(75) Inventors: Peter George Delano, Oakland, NJ (US); Andrew Wong, Philadelphia, PA (US); Michael Meehan, Glen Rock, NJ (US); Christina D'Arrigo, Hoboken, NJ (US); Annica Wayman, Morris Plains, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 0 days.

(21) Appl. No.: 12/275,636

(22) Filed: Nov. 21, 2008

(65) Prior Publication Data

US 2009/0292259 A1 Nov. 26, 2009

Related U.S. Application Data

(60) Provisional application No. 60/989,553, filed on Nov. 21, 2007.

(51) Int. Cl.
| | |
|---|---|
| *A61M 25/01* | (2006.01) |
| *A61M 25/00* | (2006.01) |
| *A61M 25/06* | (2006.01) |

(Continued)

(52) U.S. Cl.
CPC ........ *A61M 25/0102* (2013.01); *A61B 17/3401* (2013.01); *A61M 25/0097* (2013.01); *A61M 25/0136* (2013.01); *A61M 25/0606* (2013.01); *A61B 2017/00455* (2013.01);

(Continued)

(58) Field of Classification Search
CPC ............. A61M 2025/0063; A61M 2025/0175; A61M 25/0097; A61M 25/0102; A61M 25/0136; A61M 25/0606

USPC .......... 604/164.07, 164.01, 158, 165.03, 162, 604/164.06, 164.08, 165.01, 165.02, 604/165.04; 600/567, 564

See application file for complete search history.

(56) References Cited

U.S. PATENT DOCUMENTS 4,405,307 A * 9/1983 Taylor ...................... 604/165.01
4,881,551 A 11/1989 Taylor (Continued)

FOREIGN PATENT DOCUMENTS

| | | |
|---|---|---|
| CN | 1951513 A | 4/2007 |
| EP | 1661521 A1 | 5/2006 |

(Continued)

OTHER PUBLICATIONS

U.S. Appl. No. 12/275,570.

(Continued)

*Primary Examiner* — Kevin C Sirmons
*Assistant Examiner* — Shefali Patel
(74) *Attorney, Agent, or Firm* — The Webb Law Firm

(57) ABSTRACT

A hub assembly, such as for long needles, is disclosed. The hub assembly includes a needle hub having a proximal end and a distal end, having a cannula extending therethrough and protruding from the distal end, with the needle hub having a first engagement portion. The hub assembly also includes a stylet handle having a stylet extending therefrom. The stylet is adapted to be received within a portion of the cannula, with the stylet handle having a second engagement portion. An engagement of the first engagement portion of the needle hub and the second engagement portion of the stylet handle forms a positive lock in which at least a portion of one of the first and second engagement portions is held within the other of the first and second engagement portions in an unbiased state.

26 Claims, 13 Drawing Sheets

(51) Int. Cl.
*A61B 17/34* (2006.01)
*A61B 17/00* (2006.01)

(52) U.S. Cl.
CPC ............... *A61B 2017/00477* (2013.01); *A61M 2025/0063* (2013.01); *A61M 2025/0175* (2013.01)

(56) References Cited

U.S. PATENT DOCUMENTS

| | | | |
|---|---|---|---|
| 5,100,390 A | | 3/1992 | Lubeck et al. |
| 5,106,376 A | | 4/1992 | Mononen et al. |
| 5,186,712 A | * | 2/1993 | Kelso et al. ............... 604/165.03 |
| 5,250,035 A | | 10/1993 | Smith et al. |
| 5,336,191 A | | 8/1994 | Davis et al. |
| 5,425,718 A | * | 6/1995 | Tay et al. .................. 604/164.11 |
| 5,466,225 A | | 11/1995 | Davis et al. |
| 5,496,281 A | | 3/1996 | Krebs |
| 5,571,091 A | | 11/1996 | Davis et al. |
| 5,843,001 A | | 12/1998 | Goldenberg |
| 5,957,893 A | * | 9/1999 | Luther et al. .............. 604/164.01 |
| 6,520,938 B1 | * | 2/2003 | Funderburk ...... A61M 25/0097 604/162 |
| 6,558,353 B2 | | 5/2003 | Zohmann |
| 6,595,958 B1 | * | 7/2003 | Mickley ................... 604/164.01 |
| 2002/0099335 A1 | | 7/2002 | Zohmann |
| 2003/0036673 A1 | | 2/2003 | Schmidt |
| 2005/0242579 A1 | | 11/2005 | Bright et al. |

FOREIGN PATENT DOCUMENTS

| | | |
|---|---|---|
| JP | 01-146559 A | 6/1989 |
| JP | 02-099070 A | 4/1990 |
| JP | 2002-102355 A | 4/2002 |

OTHER PUBLICATIONS

U.S. Appl. No. 12/275,604.
U.S. Appl. No. 12/313,661.

* cited by examiner

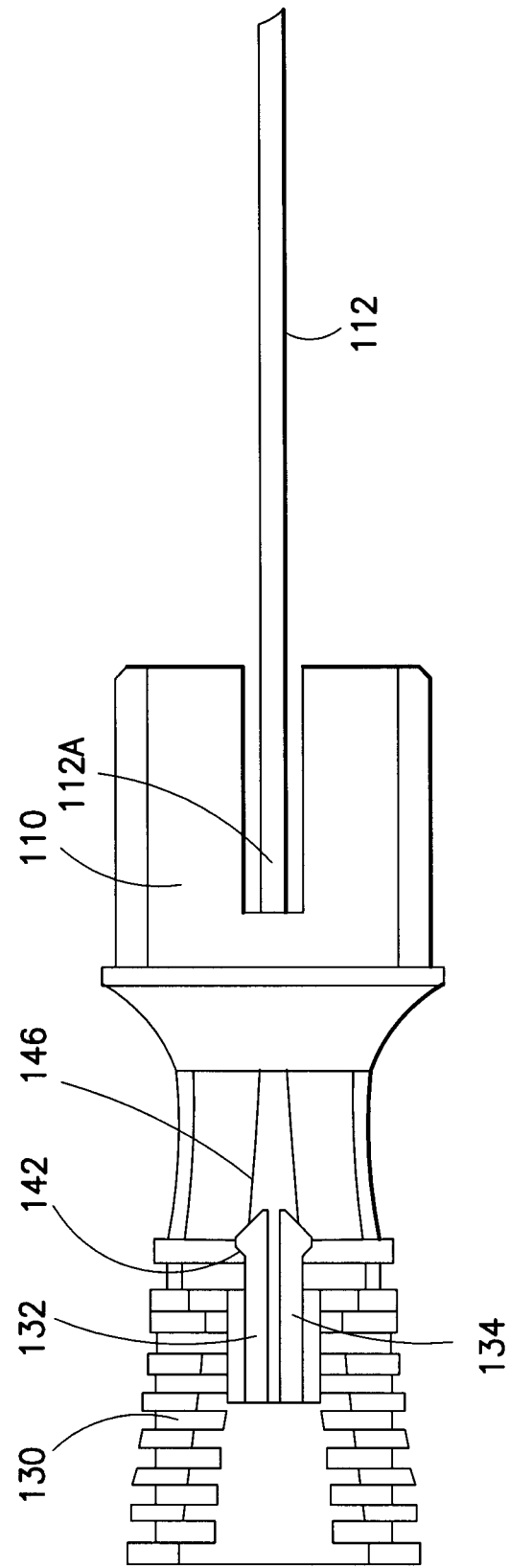

STYLET HANDLE ATTACHMENT DEVICE

CROSS REFERENCE TO RELATED APPLICATION

This application claims priority to U.S. Provisional Patent Application No. 60/989,553, filed Nov. 21, 2007, entitled "Stylet Handle Attachment Device", the entire disclosure of which is herein incorporated by reference.

BACKGROUND OF THE INVENTION

1. Field of the Invention

The present invention relates to a hub assembly for receiving a stylet and, more particularly, to a hub assembly for coupling a stylet handle having corresponding tapered mating surfaces.

2. Description of Related Art

Generally speaking, there are two basic techniques for introducing injectable medicament into the spinal area of a patient. The first, introducing spinal anesthesia into the epidural space, "epidural," and the second, introducing spinal anesthesia by penetration of the dural membrane into the subarachnoid space, "spinal" or "subarachnoid." The medicaments can be any type of liquid therapeutic material including antibiotics, steroids and the like, but generally include agents used for anesthesia and analgesia.

Delivery of the medicament into the subarachnoid space requires a penetration depth of several centimeters. Puncture of the skin and dural membrane with a needle may result in tissue coring, which can cause complications due to the presence of the tissue in the subarachnoid. In order to prevent tissue coring, a stylet formed as a solid elongated member is typically inserted within the bore of the needle and extends therein. The needle, with the stylet inserted therein, limits tissue from entering the needle. After insertion of the needle within the patient, the stylet may be partially or completely removed from the bore of the needle.

Typically, the stylet is attached to a stylet handle and the needle is attached to a needle hub. The stylet handle engages the needle hub to allow the stylet to be selectively removed from the bore of the needle during the procedure. One way for attaching the stylet handle to the needle hub is to provide a male, outwardly extending portion on the handle, and a female portion on the needle hub for receiving the male portion. An interference fit is provided between the male portion and the female portion so that a compressive force is imparted on the male portion when the stylet handle and the needle hub are engaged. In this attachment design, the assembly and removal forces of the stylet handle and the needle hub is directly related to the coefficient of friction between the male and female elements and the normal force associated with the interference fit. Also, such designs typically incorporate very small interferences between the parts on the order of 0.001 inch to 0.005 inch. Therefore, small variances in geometry and friction can have a large impact on engagement forces. Additionally, since the resultant assembly of the stylet handle and needle hub are usually stored in a stressed (i.e., engaged) state, the engagement forces change over time due to creep. This change in engagement force over time can prevent the stylet handle from adequately engaging the needle hub. Accordingly, there is a general need for a hub assembly that allows a stylet handle to be selectively coupled to a needle hub such that consistent engagement forces are provided.

SUMMARY OF THE INVENTION

In one embodiment of the present invention, a hub assembly includes a needle hub having a proximal end and a distal end, having a cannula extending therethrough and protruding from the distal end. The needle hub also includes a first engagement portion. The hub assembly also includes a stylet handle having a stylet extending therefrom. The stylet is adapted to be received within a portion of the cannula, and the stylet handle has a second engagement portion. Engagement of the first engagement portion of the needle hub and the second engagement portion of the stylet handle forms a positive lock.

In one configuration, the first engagement portion is a recess and the second engagement portion is a protrusion adapted for releasable receipt within the recess. The recess may further include a shoulder, and the protrusion may further include a restraining end which is engageable with the shoulder when the needle hub and stylet handle form a positive lock. The restraining end of the protrusion may include an insertion contact surface adjacent the distal end of the stylet handle, and a removal contact surface proximally spaced from the insertion contact surface. The insertion contact surface may extend from at least one of laterally or radially from a longitudinal axis of the protrusion and may be inclined in the direction from the distal end of the restraining end to the proximal end of the restraining end. The removal contact surface may extend from at least one of laterally or radially from the longitudinal axis of the protrusion and may be inclined in the direction from the proximal end of the retraining end to the distal end of the restraining end.

The recess of the hub assembly may also include a first portion for engaging the insertion contact surface of the protrusion during transition of the protrusion from the unlocked position to the positive lock. The recess may also include a second portion for engaging the removal contact surface of the protrusion during transition of the protrusion from the positive lock to the unlocked position. In one configuration, the protrusion may include a first beam and a second beam spaced apart from the first beam, with the second beam extending along and substantially parallel to the first beam. At least one of the first beam and the second beam is adapted to transition from one of an unlocked position and a positive lock to the other of the unlocked position and the positive lock. In a further configuration, the first beam and second beam may be deflected toward each other during transition of the protrusion from one of an unlocked position and a positive lock to the other of the unlocked position and the positive lock. Each of the first beam and the second beam may be adapted to deflect from about 0.005 inch to about 0.010 inch during transition from one of the unlocked position and the positive lock to the other of the unlocked position and the positive lock.

In a further configuration, the first beam may include an insertion contact surface adjacent the distal end of the stylet handle, and a removal contact surface proximally spaced from the insertion contact surface. The second beam may also include an insertion contact surface adjacent the distal end of the stylet handle, and a removal contact surface proximally spaced from the insertion contact surface. The recess may include a first portion for engaging the insertion contact surface of the first beam and the insertion contact surface of the second beam during transition of the protrusion from the unlocked position to the positive lock. The recess may also include a second portion for engaging the removal contact surface of the first beam and the removal contact surface of the second beam during transition of the protrusion from the positive lock to the unlocked position.

The insertion contact surface of the first beam and the insertion contact surface of the second beam may extend laterally from a longitudinal axis of the protrusion and may be inclined in opposing directions from the distal end of the restraining end to the proximal end of the restraining end. The removal contact surface of the first beam and the removal contact surface of the second beam may also extend laterally from a longitudinal axis of the protrusion and may be inclined in opposing directions from the proximal end of the restraining end to the distal end of the restraining end.

The needle hub and the stylet handle may be adapted to transition between one of an unlocked position and a positive lock and the other of the unlocked position and the positive lock, in which the protrusion is in a non-deflected orientation in both the unlocked position and the positive lock. The protrusion may be deflected against a portion of the recess during transition from one of the unlocked position and the positive lock to the other of the unlocked position and the positive lock.

In a further configuration, the first engagement portion is oriented on a first side of the cannula and the second engagement portion is oriented on a first side of the stylet, such that the needle hub and the stylet handle may only form a positive lock when the first side of the cannula and the first side of the stylet are aligned adjacent each other. At least one of engagement or disengagement of the first engagement portion the second engagement portion may produce an audible, visual, or tactual indicator evidencing one of the unlocked position or positive lock of the needle hub and the stylet handle. The needle hub may further include a transparent portion to indicate fluid flow through the needle. The transparent portion may have a substantially parabolic curvature.

In another embodiment of the present invention, a needle assembly includes a cannula having a distal end adapted to penetrate a tissue sample, a proximal end, and a lumen extending between the distal end and the proximal end. The needle assembly also includes a needle hub connected to the proximal end of the cannula, with the needle hub having a first engagement portion. The needle assembly also includes a stylet, having a distal end and a proximal end, with the stylet adapted to be received through the lumen. The needle assembly further includes a stylet handle connected to the proximal end of the stylet, with the stylet handle having a second engagement portion. Engagement of the first engagement portion and the second engagement portion forms a positive lock between the needle hub and the stylet handle such that a disengagement force required to release the positive lock is greater than a force applied to the stylet during insertion of the distal end of the cannula in the tissue sample.

In one configuration, the first engagement portion is a recess and the second engagement portion is a protrusion adapted for releasable receipt within the recess. The recess may further include a shoulder and the protrusion may further include a restraining end engageable with the shoulder when the needle hub and stylet handle form a positive lock. In a further configuration, the protrusion includes a first beam and a second beam spaced apart from the first beam, with the second beam extending along and substantially parallel to the first beam. Optionally, the first beam and the second beam are deflected toward each other during transition of the protrusion from one of an unlocked position and a positive lock to the other of the unlocked position and the positive lock.

The first beam may include an insertion contact surface adjacent the distal end of the stylet handle and a removal contact surface proximally spaced from the insertion contact surface. The second beam may also include an insertion contact surface adjacent the distal end of the stylet handle and a removal contact surface proximally spaced from the insertion contact surface. The recess may include a first portion for engaging the insertion contact surface of the first beam and the insertion contact surface of the second beam during transition of the protrusion from the unlocked position to the positive lock. The recess may also include a second portion for engaging the removal contact surface of the first beam and the removal contact surface of the second beam during transition of the protrusion from the positive lock to the unlocked position.

The needle hub and the stylet handle may be adapted to transition between one of an unlocked position and a positive lock and the other of the unlocked position and the positive lock, with the protrusion in a non-deflected orientation in both the unlocked position and the positive lock. The protrusion may be deflected against a portion of the recess during transition from one of the unlocked position and the positive lock to the other of the unlocked position and the positive lock. In a further configuration, at least one of engagement or disengagement of the first engagement portion the second engagement portion produces an audible, visual or tactual indicator evidencing one of the unlocked position or positive lock of the needle hub and the stylet handle. The disengagement force may be less than a drag force of the cannula within a human tissue sample. In one configuration, the cannula is an 18 G needle and the disengagement force may be at least greater than 0.25 lbs. The disengagement force may also be less than 0.45 lbs. In another configuration, the cannula is a 22 G needle and the disengagement force may be at least greater than 0.09 lbs. The disengagement force may also be less than 0.27 lbs. In yet a further configuration, the needle assembly may include a needle guard circumferentially disposed about a portion of the needle and at least partially disposable within a portion of the needle hub.

In yet another embodiment of the present invention, a needle assembly includes a cannula having a beveled distal end adapted to penetrate a tissue sample, a proximal end, and a lumen extending between the distal end and the proximal end. The needle assembly also includes a needle hub connected to the proximal end of the cannula, with the needle hub having a first engagement portion including a first directional indicator corresponding to the orientation of the beveled distal end of the cannula. The needle assembly also includes a stylet having a beveled distal end and a proximal end, with the stylet adapted to be received through the lumen. The needle assembly further includes a stylet handle connected to the proximal end of the stylet, with the stylet handle having a second engagement portion including a second directional indicator corresponding to the orientation of the beveled distal end of the stylet. Engagement of the first engagement portion and the second engagement portion is permitted only when the first directional indicator and the second directional indicator are provided in mating orientation.

In one configuration, mating orientation of the first directional indicator and the second directional indicator substantially aligns the beveled distal end of the stylet with the beveled distal end of the cannula. In another configuration, engagement of the first engagement portion and the second engagement portion forms a positive lock. Optionally, at least one of formation of the positive lock and disengagement of the positive lock produces an audible, visual, or tactual indicator evidencing one of the unlocked position or positive lock of the needle hub and the stylet handle.

Further details and advantages of the invention will become clear upon reading the following detailed description in conjunction with the accompanying drawing figures, wherein like parts are designated with like reference numerals throughout.

BRIEF DESCRIPTION OF THE DRAWINGS

FIG. 10 is a front view of a hub assembly having a needle engaged therewith in the coupled state in accordance with an embodiment of the present invention.

DESCRIPTION OF THE PREFERRED EMBODIMENTS

For purposes of the description hereinafter, spatial orientation terms, if used, shall relate to the referenced embodiment as it is oriented in the accompanying drawing figures or otherwise described in the following detailed description. However, it is to be understood that the embodiments described hereinafter may assume many alternative variations and embodiments. It is also to be understood that the specific devices illustrated in the accompanying drawing figures and described herein are simply exemplary and should not be considered as limiting.

Figure 8:
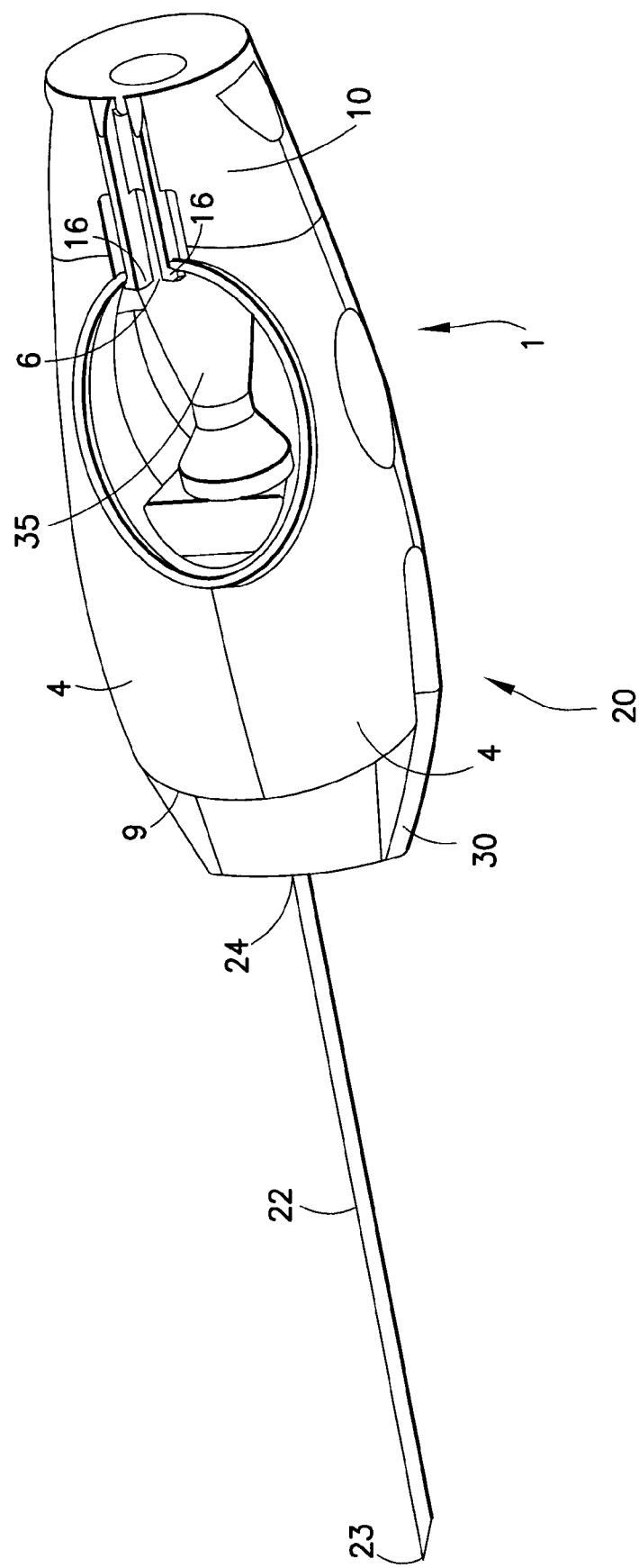
FIG. 8 is a perspective view of a hub assembly engaged with a needle in accordance with an embodiment of the present invention.

Referring to FIGS. 1-4, a hub assembly 1 of the present invention includes a needle hub 4 having a proximal end 3 and a distal end 9. The needle hub 4 may be adapted to include a cannula 22 extending at least partially therethrough, such as from the proximal end 3 to the distal end 9 and protruding a distance from the distal end 9 of the needle hub 4, as shown in FIG. 8. In one embodiment, the cannula 22 may be a "long needle" such as those adapted for use in anesthesia, spinal taps and/or epidural procedures, having a needle gauge of from 18 G to 29 G. It is also contemplated herein, however, that the hub assembly 1 may also accommodate a conventional length and gauge cannula 22 therewith. As shown specifically in FIG. 9, the cannula 22 is adapted to receive a stylet 26 at least partially therein. In one embodiment, the stylet 26 is a solid elongated shaft having an outer diameter that is smaller than an inner diameter of the cannula 22. In one configuration, the stylet 26 may have an outer diameter that is from about 0.007 inch to about 0.013 inch smaller than the inner diameter of the interior of the cannula 22. The stylet 26 may be made of any suitably rigid material, such as metal(s), metal alloy(s), and/or polymeric compositions, to enhance the stiffness of the cannula 22 when inserted therein. Referring once again to FIG. 9, the stylet 26 may be connected to a stylet handle 10, at least a portion of which is adapted for grasping or holding by a medical practitioner. In a further embodiment, the stylet handle 10 has a stylet 26 extending therefrom such that the stylet 26 is adapted to be received within a portion of the cannula 22.

Referring again to FIGS. 1-4, the needle hub 4 includes a first engagement portion 6, and the stylet handle 10 includes a second engagement portion 16. In one embodiment, the first engagement portion 6 is disposed adjacent the proximal end 3 of the needle hub 4, and the second engagement portion 16 is disposed adjacent the distal end 11 of the stylet handle 10. The needle hub 4 and the stylet handle 10 are adapted to matingly engage such that the first engagement portion 6 and the second engagement portion 16 form a positive lock therebetween. As used herein, the term "positive lock" means engagement of at least a portion of a first piece within at least a portion of a second piece wherein the first piece is held in an unbiased state within the second piece. As used herein, the term "unbiased" means a state wherein no appreciable compressive force is applied. It is noted herein that disengagement of positive lock occurs only when a sufficient peak disengagement force is applied thereto, as will be discussed herein.

In one embodiment, the first engagement portion 6 of the needle hub 4 includes a recess 6A, defined within a portion of the housing 4A of the needle hub 4, and the second engagement portion 16 of the stylet handle 10 includes a protrusion 16A adapted for releasable receipt within the recess 6A. In one embodiment, the recess 6A is formed by a notch recessed within the housing 4A of the needle hub 4. In a further configuration, a shoulder 6B is formed integral with the housing 4A of the needle hub 4 and is positioned adjacent the recess 6A. The protrusion 16A may include a restraining end 16B, shown in FIG. 2, engageable with the shoulder 6B when the first engagement portion 6 of the needle hub 4 and the second engagement portion 16 of the stylet handle 10 form a positive lock. Although the first engagement portion 6 of the needle hub 4 is depicted herein as defining a recess and the second engagement portion 16 of the stylet handle 10 is depicted herein as including a protrusion 16A, it is also contemplated herein that the first engagement portion 6 may include a protrusion, and the second engagement portion 16 may include a corresponding recess structured to allow receipt of the protrusion therein to form a positive lock. It is also contemplated herein that the first engagement portion 6 and the second engagement portion 16 may include any suitable engaging structure that forms a positive lock therebetween.

Referring again to FIGS. 1-4, in another embodiment, the protrusion 16A includes a first beam 12 and a second beam 13 spaced apart from the first beam 12, with the second beam 13 extending along and substantially parallel to the first beam 12. Each of the first beam 12 and the second beam 13 may have a first end 16B, which extends beyond the distal end 11 of the stylet handle 10 along the longitudinal axis $L_1$ of the stylet handle 10, shown in FIG. 4. Each of the first beam 12 and the second beam 13 may also have a second end 17 which is co-formed with or attached to the stylet handle 10. In this configuration, both the first beam 12 and the second beam 13 may be adapted for simultaneous releasable receipt within the recess 6A to form a positive lock.

Figure 1:
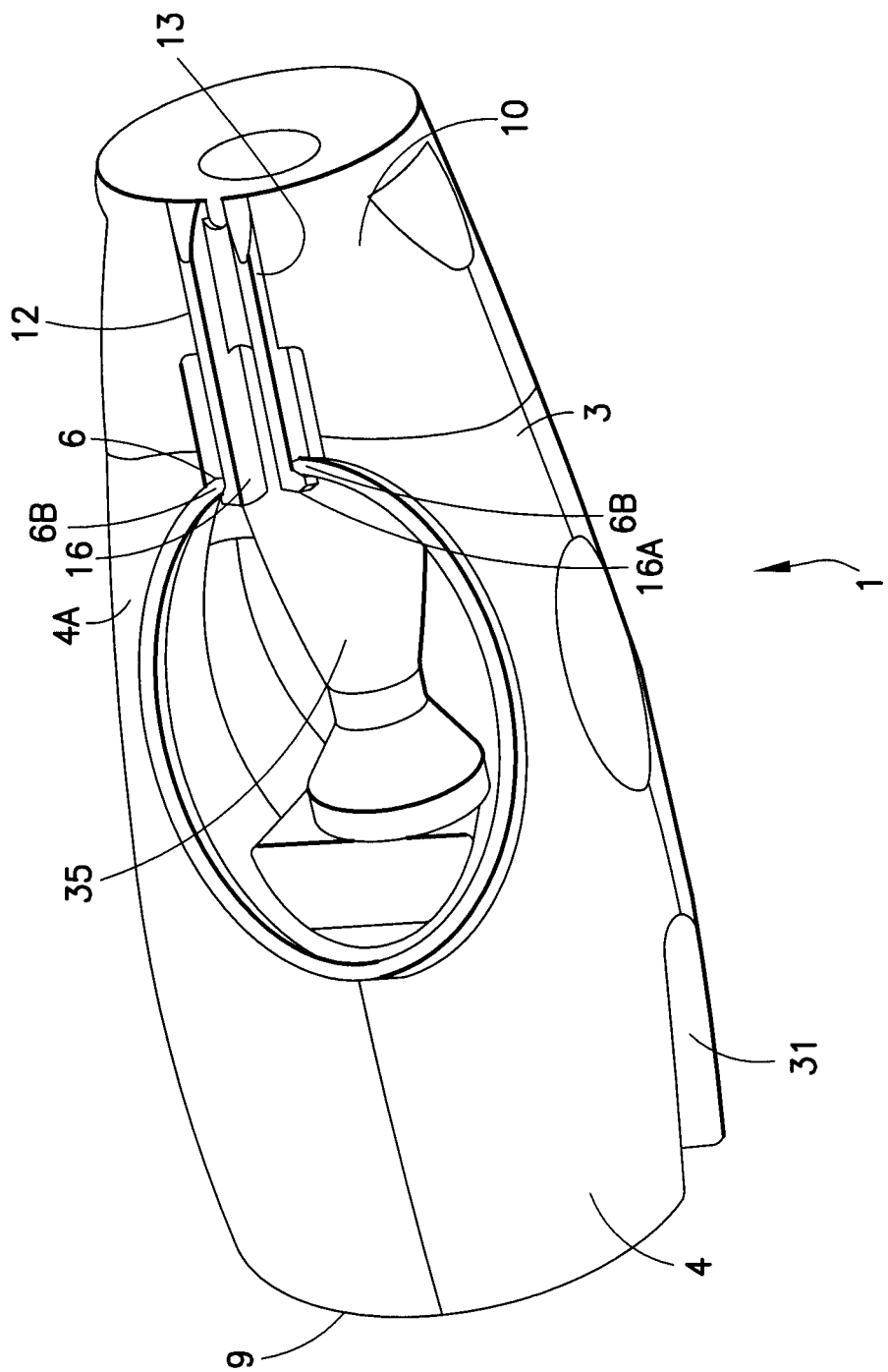
FIG. 1 is a perspective view of a hub assembly pursuant to an embodiment of the present invention.
Figure 2:
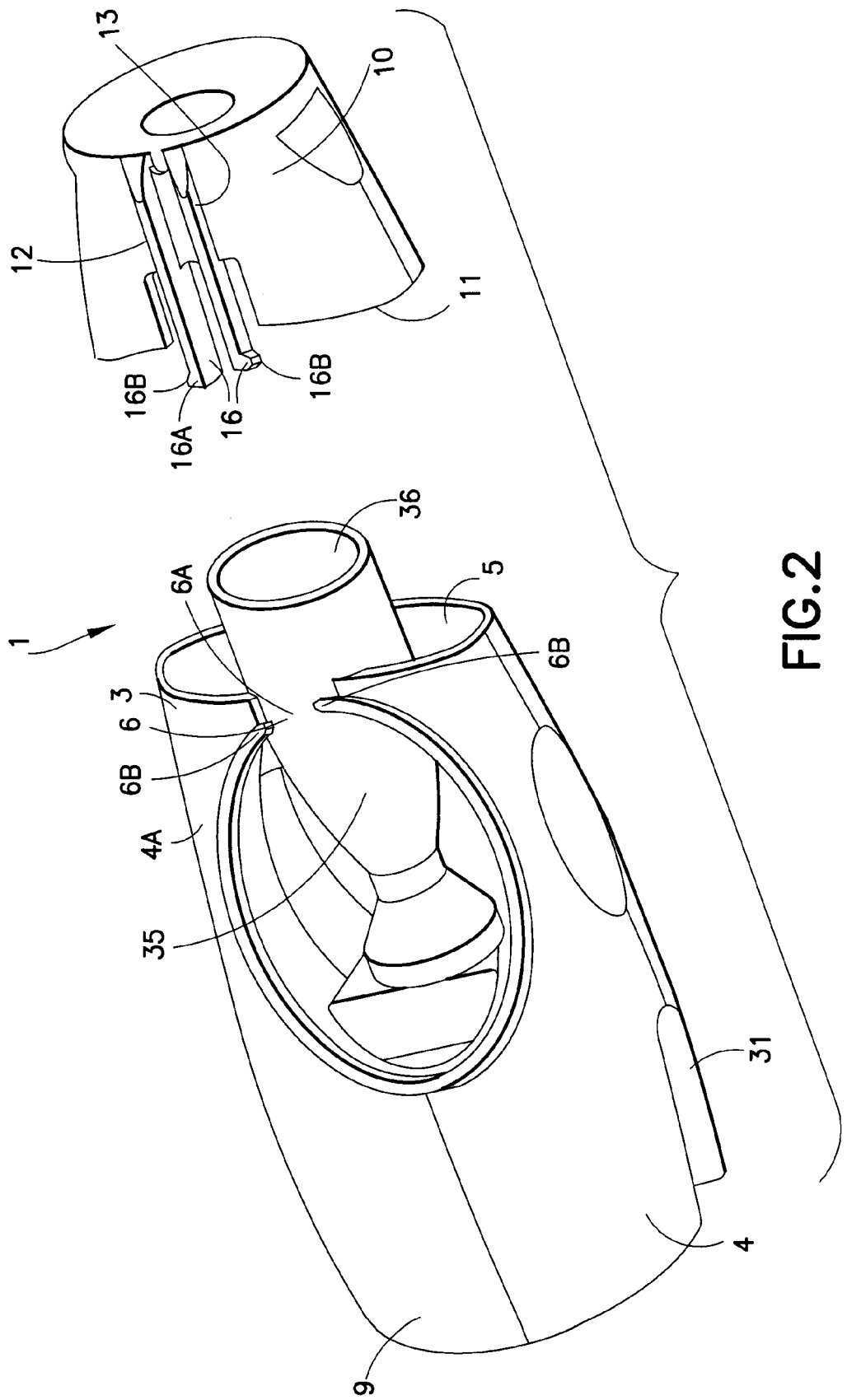
FIG. 2 is an exploded perspective view of the hub assembly shown in FIG. 1.
Figure 3:
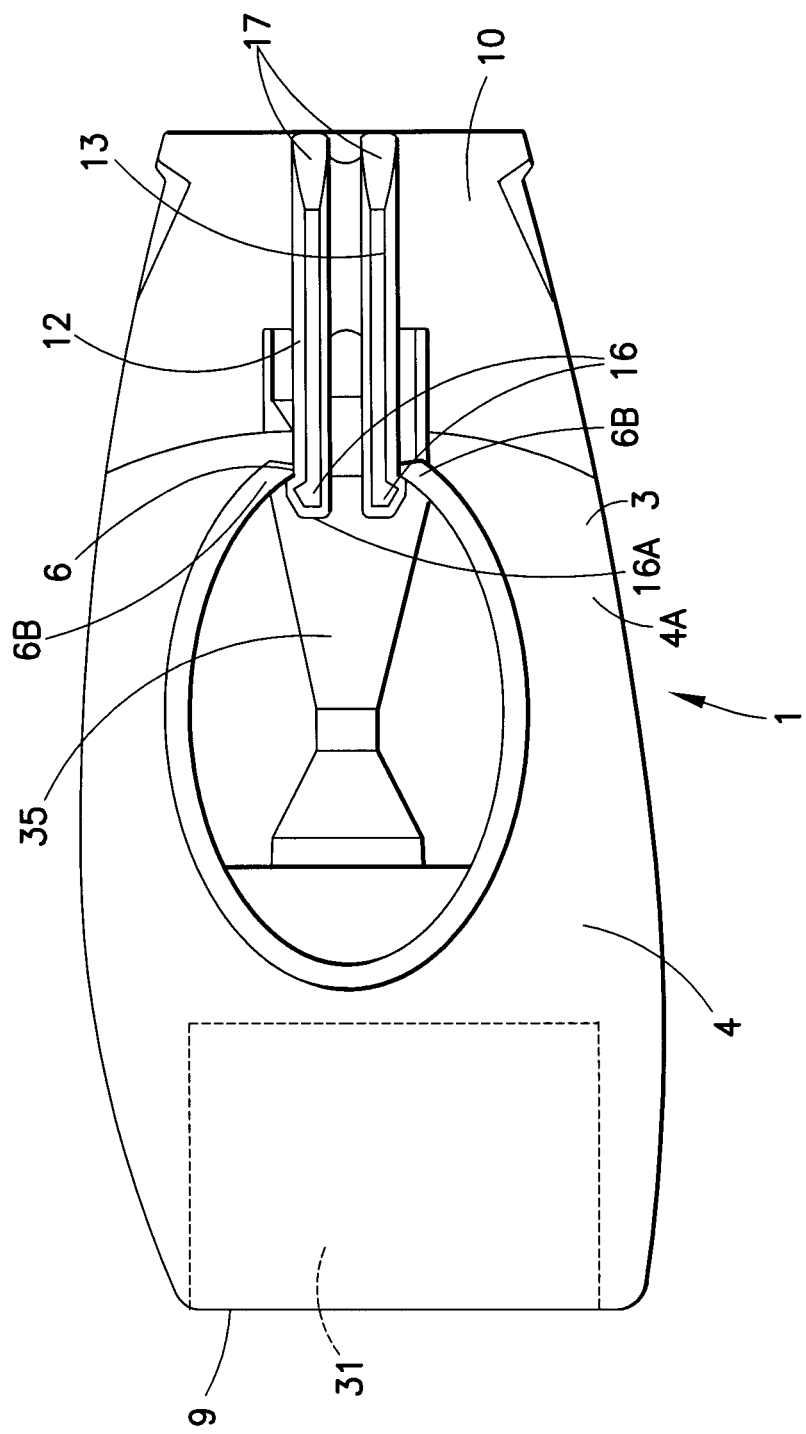
FIG. 3 is a top view of the hub assembly shown in FIG. 1.
Figure 4:
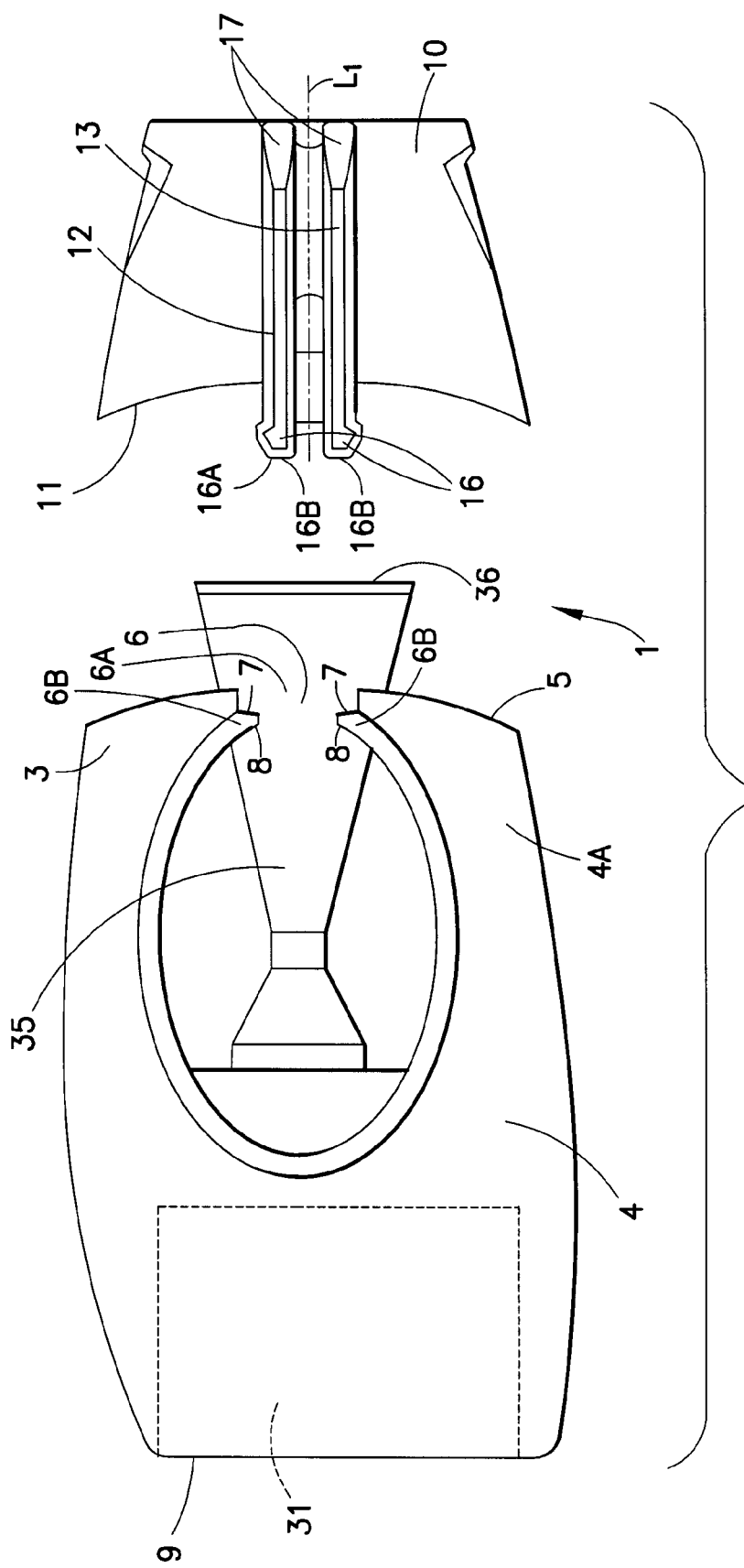
FIG. 4 is an exploded top view of the hub assembly shown in FIG. 1.
Figure 5:
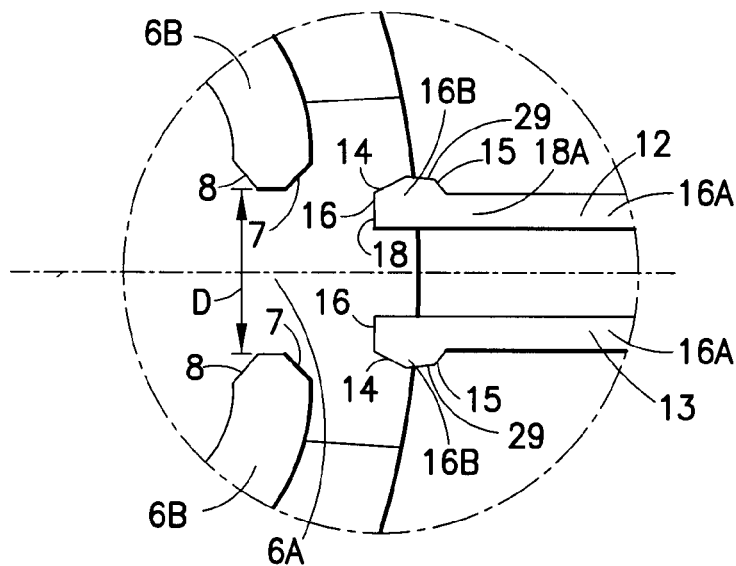
FIG. 5 is a close-up sectional top view of the hub assembly in an uncoupled state in accordance with an embodiment of the present invention.
Figure 6:
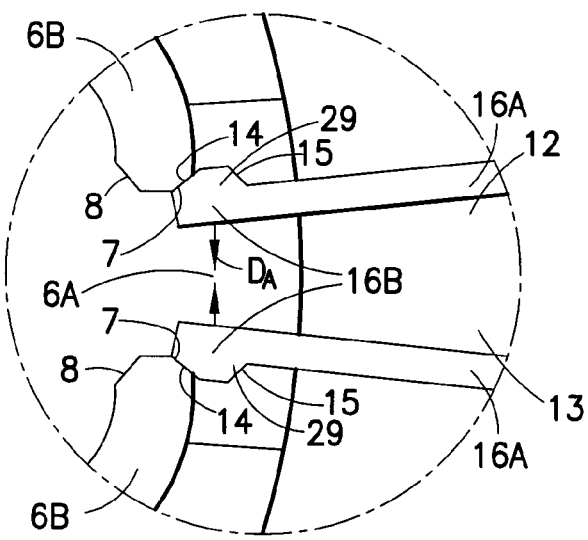
FIG. 6 is a close-up front view of the hub assembly transitioning from an uncoupled state to a coupled state in accordance with an embodiment of the present invention.
Figure 7:
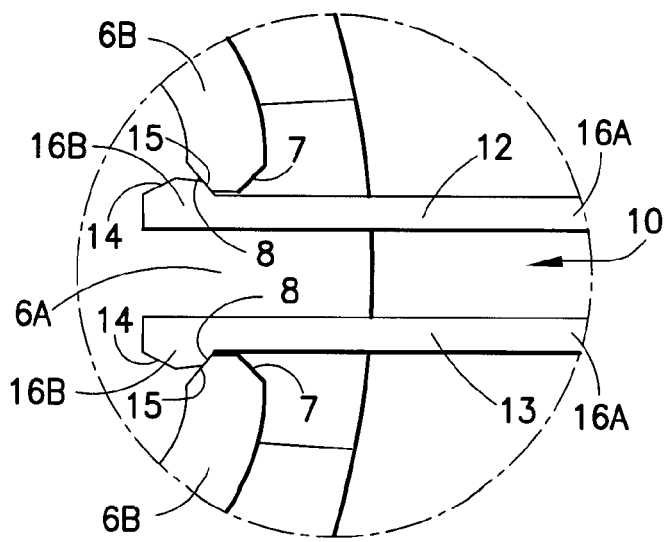
FIG. 7 is a close-up front view of the hub assembly in the coupled state in accordance with an embodiment of the present invention.

FIGS. 5-7 show a close-up engagement of the needle hub 4 and the stylet handle 10, shown in FIG. 1. Specifically, FIGS. 5-7 show a close-up transition of the first engagement portion 6 and the second engagement portion 16 from the unlocked position, shown in FIG. 5, to a deflecting position, shown in FIG. 6, to a positive lock, shown in FIG. 7.

Generally, prior to a medical procedure, such as an epidural or a spinal tap, the stylet handle 10 is in a coupled state with the needle hub 4 with the stylet 26 extending through the longitudinal aperture of the needle hub 4 and into the cannula 22. After puncturing the skin and dural membrane with the needle, the stylet handle 10 is manually disengaged from the needle hub 4 removing the stylet 26 from the cannula 22. The stylet 26 may once again be inserted within the cannula 22 prior to removal of the cannula 22 from the patient.

Referring to FIGS. 5-7, the first beam 12 and the second beam 13 of the protrusion 16A may each include a restraining end 16B. The restraining end 16B may include an insertion contact surface 14 adjacent the distal end 11 of the stylet handle 10, shown in FIG. 2, and a removal contact surface 15 spaced proximally from the insertion contact surface 14. In one configuration, the insertion contact surface 14 extends in a lateral direction from the longitudinal axis L of the protrusion 16A, shown in FIG. 5. The insertion contact surface 14 may be inclined in the direction from the distal end 18 of the restraining end 16B, shown in FIG. 5, to the proximal end 18A of the restraining end 16B, also shown in FIG. 5. In one embodiment, the insertion contact surface 14 may be inclined at about 45° from the distal end 18 to the proximal end 18A of the restraining end 16B.

In another embodiment, the removal contact surface 15 extends in a lateral direction from the longitudinal axis L of the protrusion 16, shown in FIG. 5. The removal contact surface 15 may be inclined in the direction from the proximal end 18A of the restraining end 16B, shown in FIG. 5, to the distal end 18 of the restraining end 16B, also shown in FIG. 5. In one embodiment, the removal contact surface 15 may be include at about 45° from the proximal end 18A to the distal end 18 of the restraining end 16B. In another embodiment, the insertion contact surface 14 and the removal contact surface 15 may be separated from each other by a neck portion. In a further configuration, the insertion contact surface 14 and the removal contact surface 15 define an outwardly extending protrusion 29 on each of the first beam 12 and the second beam 13. In yet a further configuration, the outwardly extending protrusion 29 of the first beam 12 extends laterally or radially from the longitudinal axis L in an orientation that is a mirror image from the outwardly extending protrusion 29 of the second beam 13.

Referring again to FIGS. 5-7, the recess 6A includes a shoulder 6B having a first portion 7 for engaging the insertion contact surface 14 of the protrusion 16A during transition of the protrusion 16A from the unlocked position, shown in FIG. 5 to the positive lock, shown in FIG. 7. The shoulder 6B of the recess 6A also includes a second portion 8 for engaging the removal contact surface 15 of the protrusion 16A during transition of the protrusion 16A from the positive lock to the unlocked position. The shoulder 6B of the recess 6A may also include a first portion 7 and second portion 8 corresponding to each of the first beam 12 and the second beam 13. In an alternative embodiment, at least one of the recess 6A and the protrusion 16A includes at least one of an angled insertion contact surface 14 and an angled removal contact surface 15. In another embodiment, only one of the recess 6A and the protrusion 16A include at least one of an angled insertion contact surface 14 and an angled removal contact surface 15. In yet another embodiment, one of the recess 6A and the protrusion 16A include at least one of an angled insertion contact surface 14 and an angled removal contact surface 15, and the other of the recess 6A and the protrusion 16A include at least one of a blunted or squared insertion contact surface 14 and a blunted or squared removal contact surface 15.

During engagement or disengagement of the needle hub 4 and the stylet handle 10, shown in FIG. 1, the protrusion 16A is deflected against a portion of the recess 6A during transition from one of the unlocked position and the positive lock to the other of the unlocked position and the positive lock. In one configuration, at least one of the first beam 12 and the second beam 13 are adapted to transition from one of an unlocked position, shown in FIG. 5, to a positive lock, shown in FIG. 7. In one configuration, the first beam 12 and the second beam 13 are deflected toward each other during transition, as shown in FIG. 6.

When the stylet handle 10 is in an unengaged position with respect to the needle hub 4, the first engagement portion 6 and the second engagement portion 16 are in the unlocked position, shown in FIG. 5. In the unlocked position, the first beam 12 and the second beam 13 of the protrusion 16A are in a non-deflected and unbiased orientation. During engagement of the stylet handle 10 and the needle hub 4, the first engagement portion 6 and the second engagement portion 16 contact each other, as shown in FIG. 6. In the contact position the protrusion 16A, such as the first beam 12 and the second beam 13, are deflected against a portion of the shoulder 6B or recess 6A and become biased. In one configuration, the insertion contact surface 14 of the protrusion 16A engages the first portion 7 of the shoulder 6B and biases the protrusion 16A against the shoulder 6B. In another configuration, the insertion contact surface 14 of the first beam 12 and the insertion contact surface 14 of the second beam 13 engage the first portion 7 of the shoulder 6B, biasing both the first beam 12 and the second beam 13 toward the longitudinal axis L, shown in FIG. 5. As the stylet handle 10 is coupled with the needle hub 4, shown in FIG. 7, the protrusion 16A is engaged within the recess 6A, and the first engagement portion 6 and the second engagement portion 16 are in positive lock. In the positive lock, the protrusion 16A is in a non-deflected and unbiased orientation. Specifically, the first beam 12 and the second beam 13 are at least partially received within the recess 6A and each of the first beam 12 and the second beam 13 are unbiased.

Due to the relatively long length of the first beam 12 and the second beam 13 with respect to the corresponding width of the first beam 12 and the second beam 13, the restraining end 16B of the first beam 12 and the restraining end 16B of the second beam 13 can deflect a distance DA which minimizes the effect of small geometric variations on the interface forces of the hub assembly 1. In a further configuration, the first beam 12 and the second beam 13 are adapted to deflect a distance DA of from about 0.005 inch to about 0.010 inch toward the longitudinal axis L of the protrusion 16A during transition from one of the unlocked position to the positive lock. It is noted herein, that the distance D of the recess 6A is dimensioned to correspond to the distance between the first beam 12 and the second beam 13, such that a resistive interference fit exists between the restraining end 16B and the shoulder 6B in the positive lock. In one configuration, a resistive interference exists between the removal contact surface 15 of the protrusion 16A and the second portion 8 of the shoulder 6B of the recess 6A. In a further configuration, a resistive interference exists between the removal contact surface 15 of the first beam 12 and the second portion 8 of the shoulder 6B, and a resistive interference exists between the removal contact surface 15 of the second beam 13 and the second portion 8 of the shoulder 6B. As used herein, the term "resistive interference" means that when a force is applied to at least one of the needle hub 4 and the stylet handle 10 in a direction substantially along the longitudinal axis $L_1$, shown in FIG. 4, physical contact between a portion of the first engagement portion 6 and a portion of the second engagement portion 16 prevents disengagement of the needle hub 4 and the stylet handle 10 until a disengagement force is applied thereto. It is noted herein that "resistive interference" exists between the stylet handle 10 and the needle hub 4 only during the act of engagement therewith or disengagement therefrom. Although the insertion contact surface 14 and the removal contact surface 15 are depicted herein as opposing inclined planes forming an outwardly extending protrusion 29, other shapes may be selected for the insertion contact surface 14 and the removal contact surface 15, such as rounded portions, provided the protrusion 16A and the recess 6A have a resistive interference in the positive lock. In a further embodiment, the formation of the positive lock and/or the disengagement of the positive lock produces an audible, visual, or tactile indicator evidencing the positive lock or the unlocked position, respectively. Example indicators include a "popping" sound, a "clicking" sound, a color change or evidence of color, or a tactile ridge or recessed formed with the needle assembly 20.

To disengage the stylet handle 10 from the needle hub 4, a sufficient disengagement force is applied to the stylet handle 10 a substantially longitudinal direction away from the proximal end 5 of the needle hub 4 such that the removal contact surface 15 of the protrusion 16A, such as the removal contact surfaces 15 of each of the first beam 12 and the second beam 13, engages the second section 8 of the recess 6A to first place the protrusion 16A in a deflected position, and subsequently place the protrusion 16A in an unlocked position.

Figure 9:
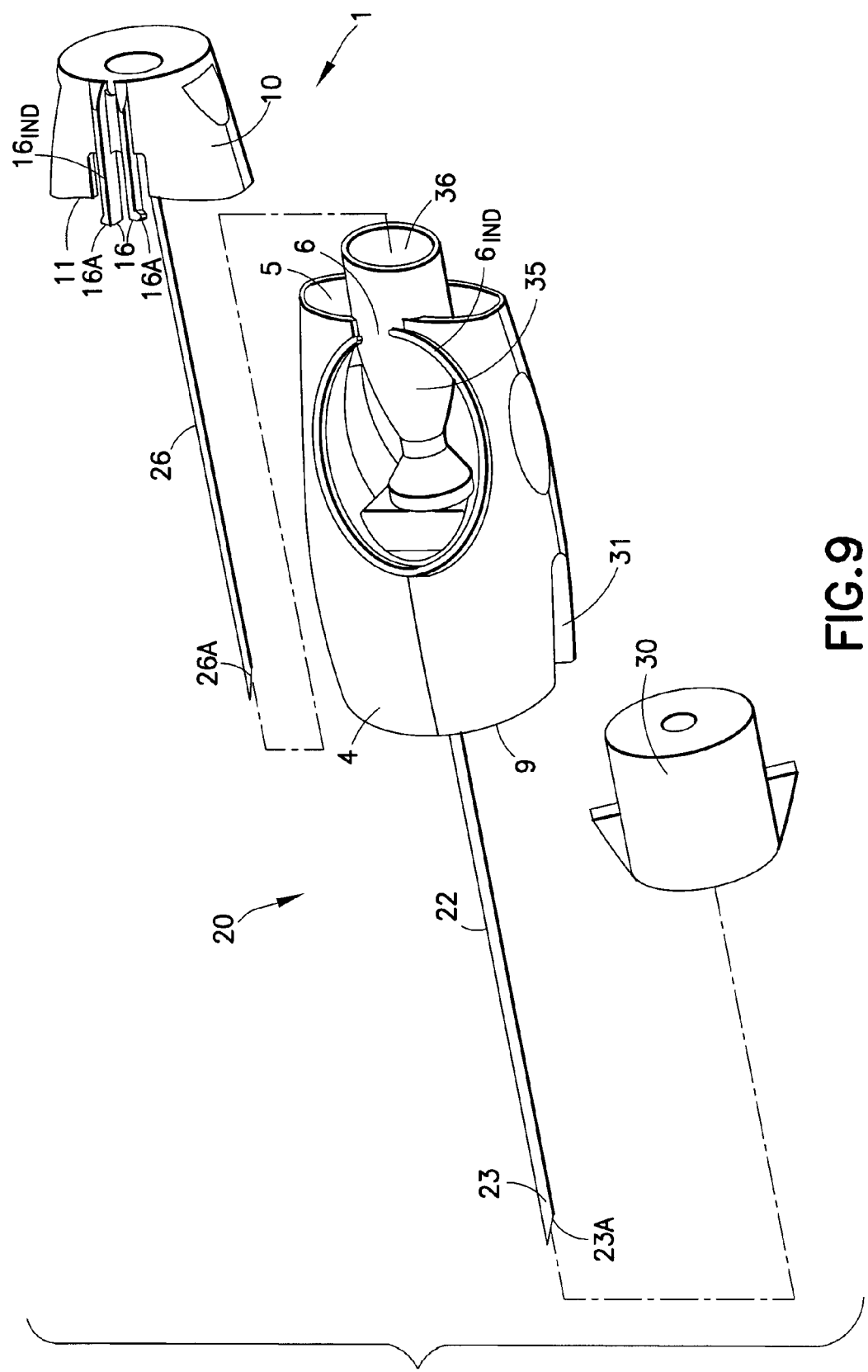
FIG. 9 is an exploded perspective view of a hub assembly having a needle engaged therewith and a needle guard in accordance with an embodiment of the present invention.

In one embodiment, the disengagement force required to remove the stylet handle 10, and stylet 26 attached thereto, from the needle hub 4, shown in FIG. 1, is greater than the force applied to the stylet bevel face 26A of the needle assembly 20, shown in FIG. 9, during penetration of human tissue. If the disengagement force required to remove the stylet handle 10 from the needle hub 4 is less than the force applied to the stylet bevel face 26A, shown in FIG. 9, during insertion of the needle assembly 20 into human tissue, then the stylet handle 10 may become prematurely disengaged from the needle hub 4, resulting in a proximal shift of the stylet 26, from within the cannula 22 to a location at least partially external to the cannula 22. One of the purposes of disposing a stylet 26 within the interior or lumen of a cannula 22 is to prevent tissue coring during insertion. If the stylet 26 prematurely pops from the interior of the cannula 22, then tissue may enter the interior of the cannula 22 and cause blockages and/or contamination within the cannula 22. In certain situations, tissue cores entering the interior of the cannula 22 from the skin surface which are deposited in the subarachnoid space of the spinal cord by the cannula 22 can develop into intraspinal epidermoid tumors. The force applied to the stylet 26 during insertion depends on a number of factors, including the thickness and toughness of the skin sample and the cannula gauge. In one embodiment, the penetration force of an 18 G spinal needle into human skin at speeds ranging from 0.1 to 2 ips is from about 0.7 lbs to 0.85 lbs. For a stylet 26 having a total bevel face 26A of 30%, shown in FIG. 9, the force applied to the stylet 26 is about 0.25 lbs. Accordingly, for an 18 G cannula, the disengagement force required to remove the stylet handle 10 from the needle hub 4, thereby disengaging the first engagement portion 6 and the second engagement portion 16, is at least greater than 0.25 lbs. In another embodiment, the penetration force of a 22 G spinal needle into human skin at speeds ranging from 0.1 to 2 ips is about 0.3 lbs. For a stylet 26 having a total bevel face 26A of 30%, shown in FIG. 9, the force applied to the stylet 26 is about 0.09 lbs. Accordingly, for a 22 G cannula, the disengagement force required to remove the stylet handle 10 from the needle hub 4, thereby disengaging the first engagement portion 6 and the second engagement portion 16, is at least greater than 0.09 lbs.

In another embodiment, the disengagement force required to remove the stylet handle 10, and the stylet 26 attached thereto, from the needle hub 4, shown in FIG. 1, is less than the drag force to remove the cannula 22 from a patient once the cannula 22 has been inserted. Once a cannula 22 having a stylet 26 disposed therein, as shown in FIG. 9, has been inserted into the tissue of a patient, the stylet 26 is typically removed from the cannula 22 to allow sampling of bodily fluids therethrough and/or delivery of therapeutic and/or diagnostic fluids therethrough. In order to prevent removal of the cannula 22 from the patient, or wiggling of the cannula 22 within the patient, during disengagement of the stylet handle 10 and the needle hub 4, the disengagement force required to remove the stylet handle 10 from the needle hub 10 must be less than the drag force required to remove the cannula 22 from a human tissue sample. The drag force of a cannula 22 in human tissue depends on a number of factors including the cannula gauge. In one embodiment, the drag force required to remove an 18 G cannula from a patient is about 0.45 lbs. Accordingly, for an 18 G cannula, the disengagement force required to remove the stylet handle 10 from the needle hub 4, thereby disengaging the first engagement portion 6 and the second engagement portion 16, is less than 0.45 lbs. In another embodiment, the disengagement force required to remove the stylet handle 10 from the needle hub 4, thereby disengaging the first engagement portion 6 and the second engagement portion 16 for an 18 G cannula is at least greater than 0.25 lbs and less than 0.45 lbs. In another embodiment, the drag force required to remove a 22 G cannula from a patient is about 0.27 lbs. Accordingly, for a 22 G cannula, the disengagement force required to remove the stylet handle 10 from the needle hub 4, thereby disengaging the first engagement portion 6 and the second engagement portion 16, is less than 0.27 lbs. In another embodiment, the disengagement force required to remove the stylet handle 10 from the needle hub 4, thereby disengaging the first engagement portion 6 and the second engagement portion 16 for a 22 G cannula is at least greater than 0.09 lbs and less than 0.27 lbs.

Figure 9A:
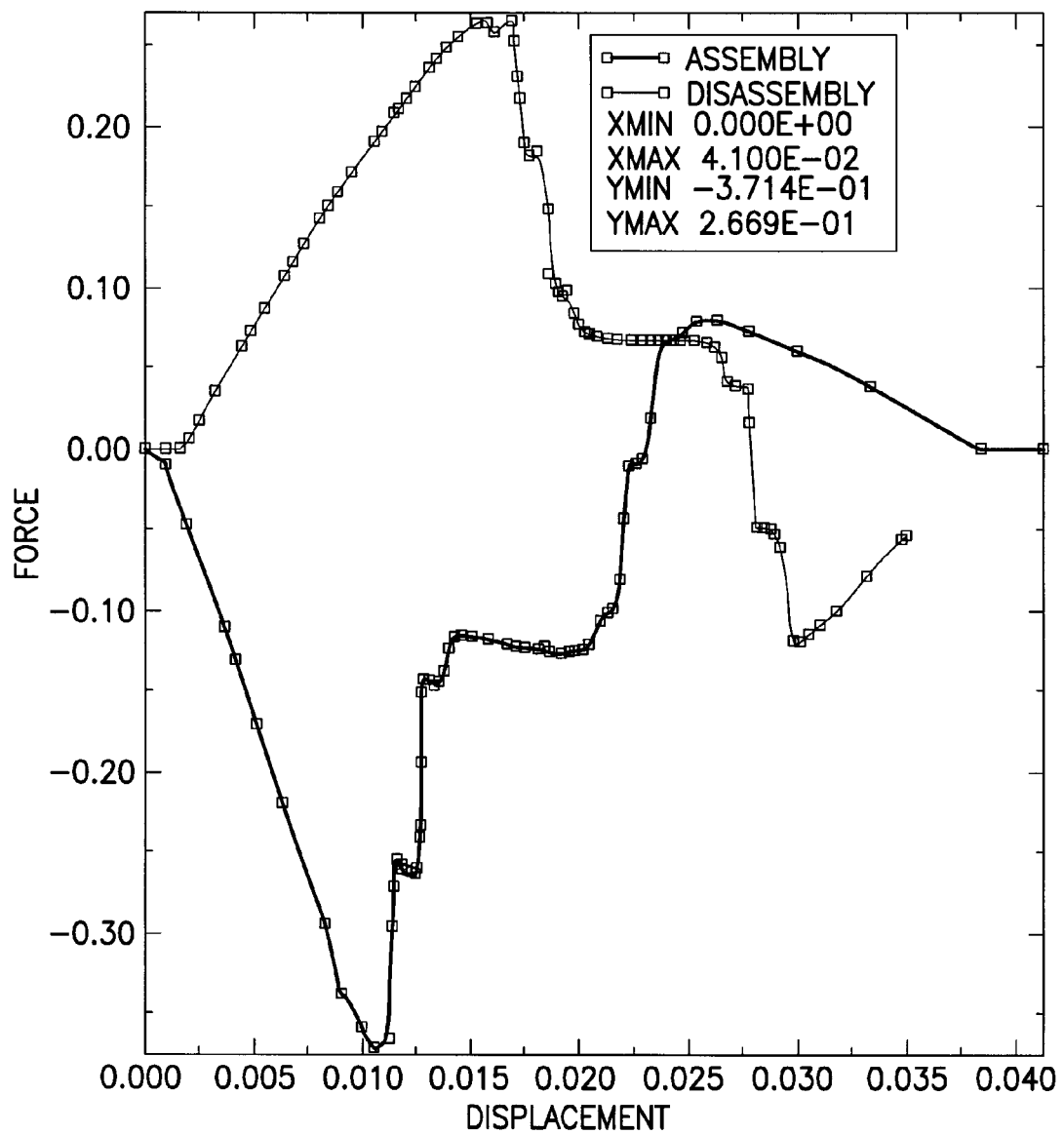
FIG. 9A is a graphic representation of the disengagement force and engagement force required to engage a stylet handle with the needle hub for an 18 G cannula.

FIG. 9A is a graphic representation of the disengagement force (disassembly) required to remove a stylet handle from a needle hub attached to an 18 G cannula. FIG. 9A also illustrates the engagement force (assembly) required to engage a stylet handle with a needle hub attached to an 18 G cannula. As seen in FIG. 9A, the disengagement force is less than the engagement force. FIG. 9A shows that both the engagement and disengagement force of the present invention are greater than 0.25 lbs and less than 0.5 lbs. Accordingly, the present invention provides improved functionality as compared to conventional stylet engagements. Although the engagement force may be determined in part on user preference, the engagement force should not be great enough, such as above 0.5 lbs force, to cause excessive movement or vibration of the assembly 20, and especially the cannula tip 23, during reinsertion in sensitive procedures. The engagement force profile is not solely dependent on the coefficient of friction, interference between the first engagement portion 6 and the second engagement portion 16, and beam stiffness, but also depends on the contact angle between the insertion contact surface 14 and the first portion 7 of the recess 6A. In certain configurations, the stiffness of the first beam 12 and the second beam 13 can also be adjusted to control the amount of force needed to engage the stylet handle 10 with the needle hub 4. Accordingly, the present invention is less dependent on friction and variations in the coefficient of friction between the parts as compared to conventional hub assemblies. Furthermore, when the stylet handle 10 is coupled to the needle hub 4 there is no bias or deflection in the protrusion 16A, such as in the first beam 12 and the second beam 13, such that the influences of strain relaxation over time is substantially eliminated.

Referring to FIGS. 8-9, the assembled needle assembly 20, having a needle hub 4 engaged with a cannula 22, and a stylet handle 10 engaged with a stylet 26 is depicted. As shown in FIG. 8, in the engaged position, the first engagement portion 6 and the second engagement portion 16 form a positive lock in which the second engagement portion 16 is held in an unbiased state within a portion of the first engagement portion 6. In this configuration, the first engagement portion 6 is disposed adjacent the proximal end 5 of the needle hub 4. A distal end 9 of the needle hub 4 may include a cavity 31 dimensioned to at least partially correspond to the shape and geometry of a needle guard 30. In one configuration, the cavity 31 is sized and dimensioned to at least partially receive a needle guard 30 therein. The needle guard 30 may be circumferentially disposed about a portion of the cannula 22, and may be transitionable from a first position in which the distal tip 23 of the cannula 22 is exposed, to a second position in which the distal tip 23 of the cannula 22 is shielded to prevent accidental contact therewith.

Figure 13:
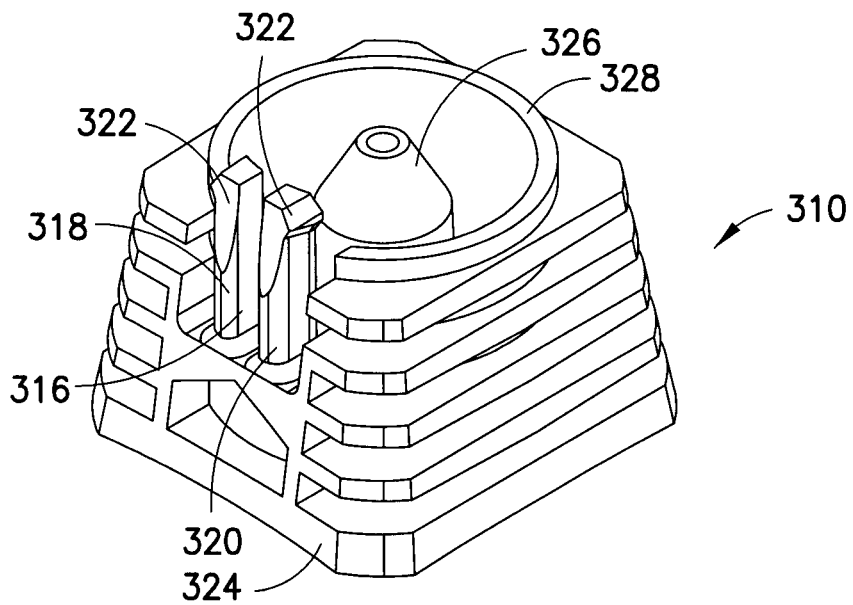
FIG. 13 is a perspective view of a stylet handle in accordance with an embodiment of the present invention.
Figure 14:
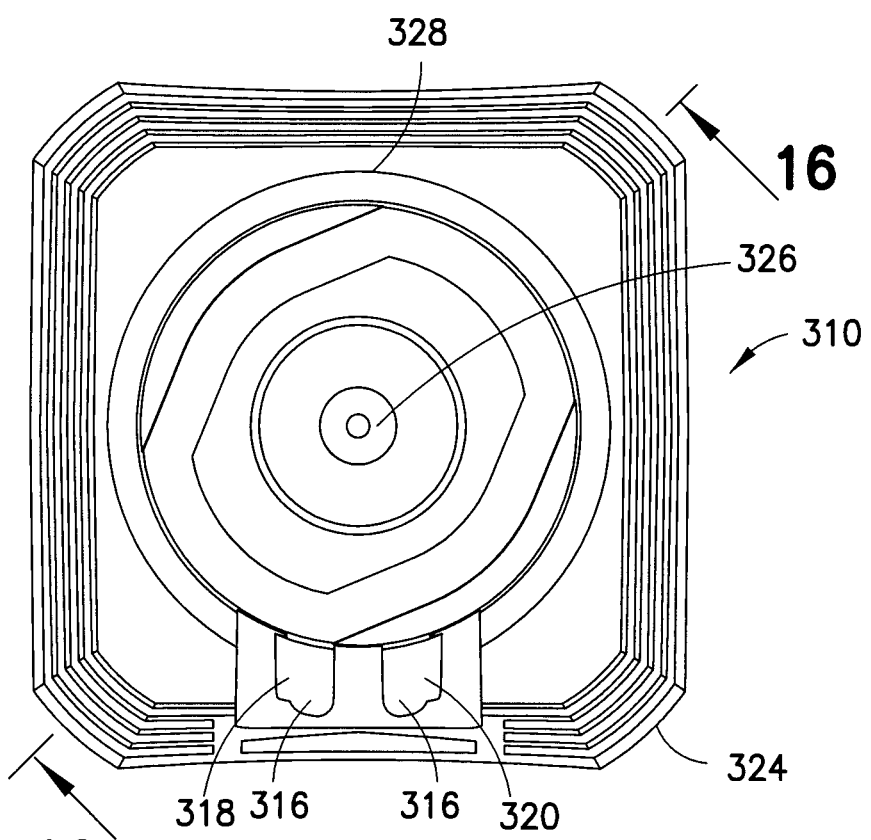
FIG. 14 is a top view of the stylet handle of FIG. 13.
Figure 15:
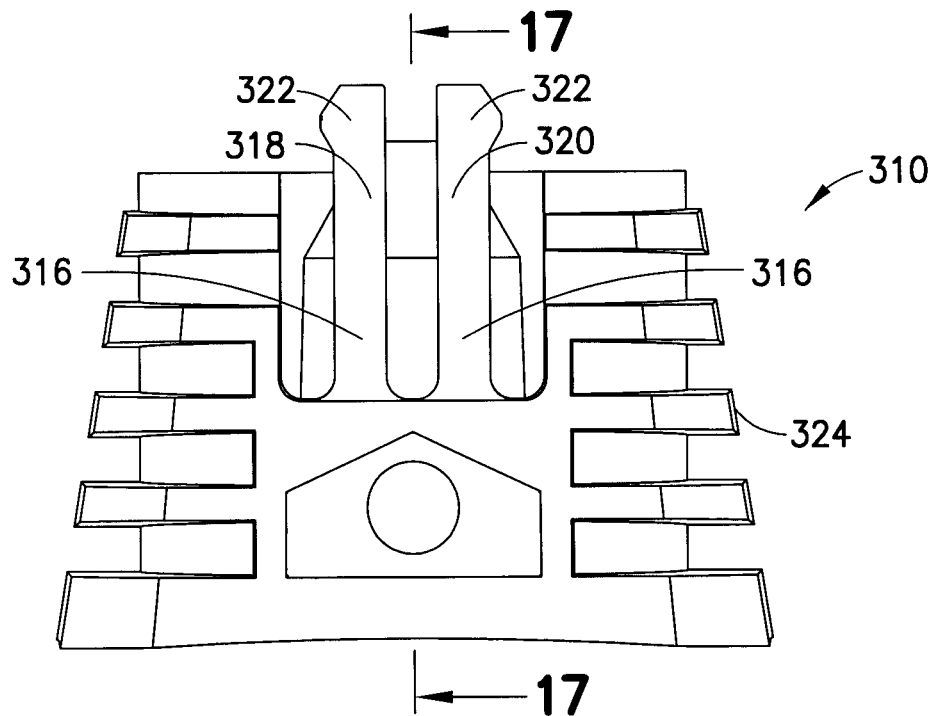
FIG. 15 is a front view of the stylet handle of FIG. 13.
Figure 16:
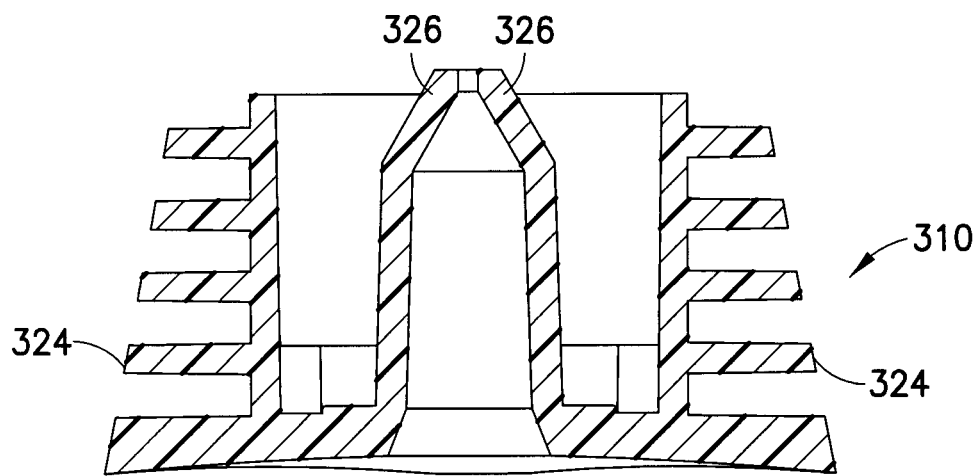
FIG. 16 is a close-up sectional side view of the stylet handle of FIG. 13 taken along line 16-16 of FIG. 14.
Figure 17:
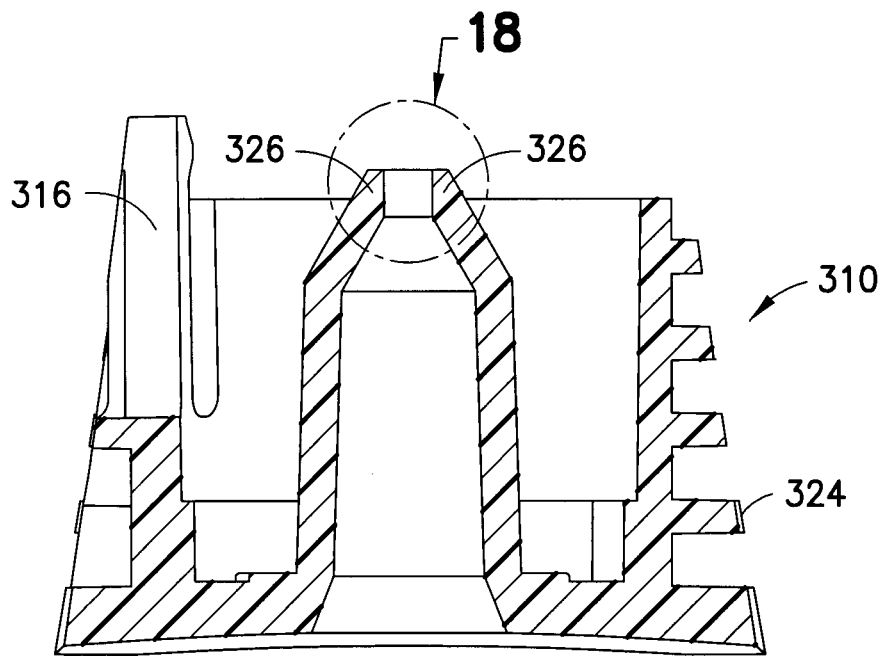
FIG. 17 is a side view of the stylet handle of FIG. 13 taken along line 17-17 of FIG. 15.
Figure 18:
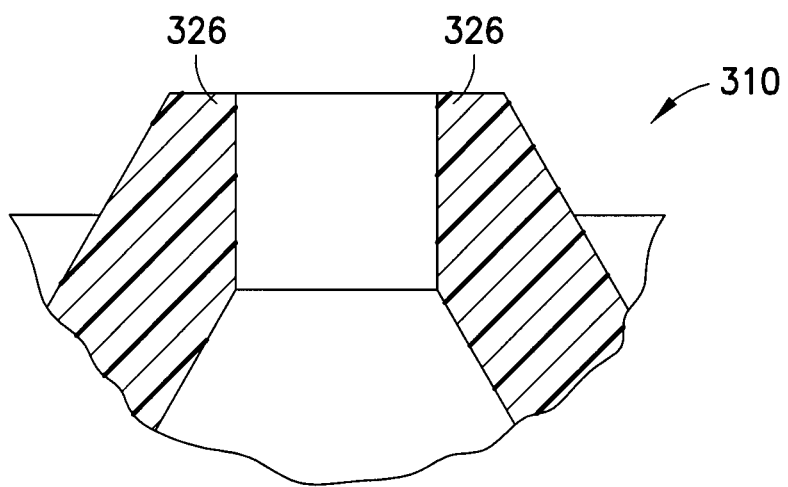
FIG. 18 is a close-up sectional view of the inner cone of the stylet handle of FIG. 13 taken along sectional line 18 of FIG. 15.

The needle hub 4 may also include a hollow, conically-shaped transparent portion 35 disposed within the needle hub 4 and viewable from the exterior of the needle hub 4 to detect the presence of fluid therein. An open end 36 of the transparent portion may extend proximally of the needle hub 4 for engagement by a corresponding portion of the stylet handle 10, such as stylet receiving port 326, shown in FIG. 13. The transparent portion 35 may allow for the detection of fluid, such as spinal fluid, therein after insertion within a patient. In one embodiment, the transparent portion 35 may include a substantially parabolic curvature to provide improved visualization of a fluid disposed therein.

Referring once again to FIG. 9, the needle hub 4 of the needle assembly 20 may also include a first engagement portion 6 having a first directional indicator $6_{Ind}$ which corresponds to the orientation of the bevel 23A of the distal tip 23 of the cannula. The directional indicator $6_{Ind}$ may include a visual or tactile indication on a portion of the housing of the needle hub 4. The directional indicator $6_{Ind}$ may also include a feature recessed into or raised from a portion of the housing of the needle hub 4, such as the recess 6A positioned with a specific location of the housing of the needle hub 4. The stylet handle 10 of the needle assembly 20 may also include a second engagement portion 16 having a second directional indicator $16_{Ind}$ which corresponds to the orientation of the bevel 26A of the stylet 26. The directional indicator $16_{Ind}$ may include a visual or tactile indication on a portion of the stylet handle 10. The directional indicator $16_{Ind}$ may also include a feature recessed into or raised from a portion of the stylet handle 10, such as the protrusion 16A, positioned with a specific location of the stylet handle 10. Engagement of the first engagement portion 6 and the second engagement portion 16 is permitted only when the first directional indicator $6_{Ind}$ and the second directional indicator $16_{Ind}$ are provided in mating orientation. As used herein, the term "mating orientation" means the first directional indicator and the second directional indicator are aligned such that at least a portion of the first engagement portion engages at least a portion of the second engagement portion.

Mating orientation substantially aligns the bevel 23A of the cannula 22 and the bevel 26A of the stylet 26. In one configuration, a portion of at least one of the first directional indicator $6_{Ind}$ and the second directional indicator $16_{Ind}$ physically restricts engagement of the first engagement portion 6 and the second engagement portion 16 unless the first directional indicator $6_{Ind}$ and the second directional indicator $16_{Ind}$ are aligned. Proper alignment of the bevel 26A of the stylet 26 and the bevel 23A of the cannula 22 can be critical during reinsertion of the stylet 26 within the cannula 22 to prevent the bevel 26A of the stylet 26 from extending beyond the bevel 23A of the cannula 22. In a further embodiment, the first engagement portion 6 may be oriented on a first side of the cannula 22 and the second engagement portion 16 may be oriented on a first side of the stylet 26, such that the needle hub 4 and the stylet handle 10 may form a positive lock only when the first side of the cannula 22 and the first side of the stylet 26 are aligned adjacent each other.

Figure 11:
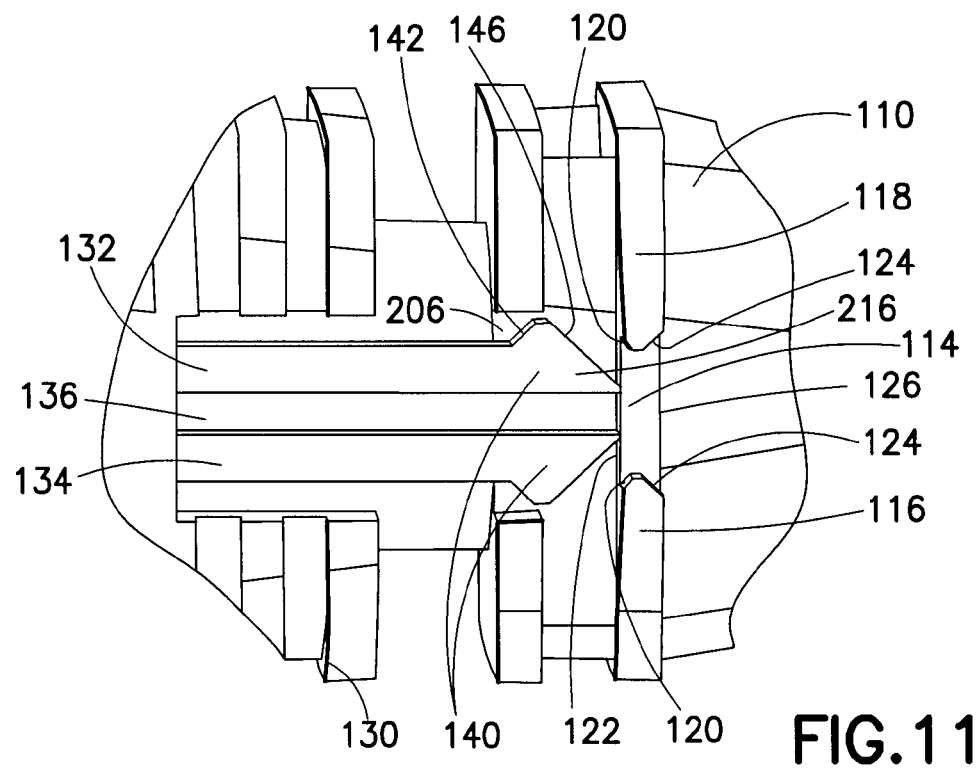
FIG. 11 is a perspective close-up view of the hub assembly in the uncoupled state in accordance with an embodiment of the present invention.
Figure 12:
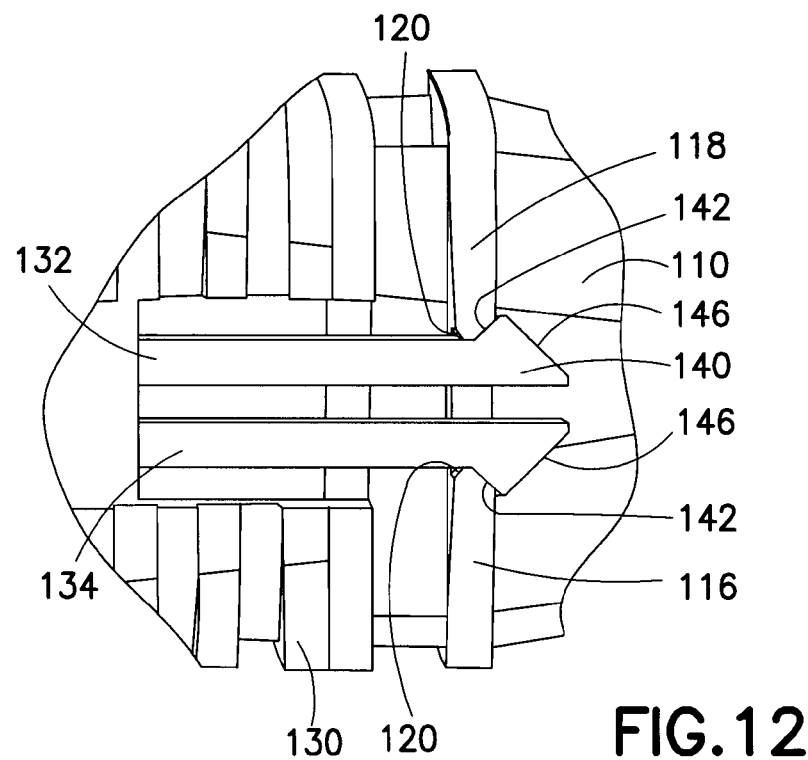
FIG. 12 is a perspective close-up view of the hub assembly in the coupled state in accordance with an embodiment of the present invention.

In an alternative embodiment of the present invention, as shown in FIGS. 10-12, a needle hub 110 adapted for engagement with a proximal non-patient end 112A of a needle cannula 112 is provided. The needle hub 110 includes a first engagement portion 206, such as recess portion 114, bordered by a first member 116 and a second member 118. Each of the first member 116 and the second member 118 include a first portion 120 adjacent an open first end 122 of the recess portion 114. Each of the first member 116 and the second member 118 also include a second portion 124 adjacent a second end 126 of the recess portion 114. A stylet handle 130 having a second engagement portion 216, such as a first beam 132 and a second beam 134 is also provided. The first beam 132 and the second beam 134 are secured within the stylet handle 130 at a first end 136. Each of the first beam 132 and the second beam 134 may include a restraining end 140. The restraining end 140 may also include a removal contact surface 142 adjacent the second end 144, and an insertion contact surface 146 disposed adjacent the first end 136.

During engagement of the stylet handle 130 and the needle hub 110, the insertion contact surface 146 of the first beam 132 and the second beam 134 may engage the first portion 120 of first member 116 and second member 118 of the needle hub 110. As the stylet handle 130 is advanced toward the needle hub 110, the insertion contact surface 146 and first portion 120 are tapered to correspondingly cam thereagainst and bias the first member 116 and the second member 118 towards each other. Once the restraining end 140 of the first beam 132 and the restraining end 140 of the second beam 134 have passed through the recess portion 114, the removal contact surface 142 of the first beam 132 and the second beam 134 are engaged against the corresponding second portion 124 of the first member 116 and the second member 118 in an unbiased state. Therefore, in the engaged position, the stylet handle 130 is not biased or pre-loaded within the needle hub 110.

During disengagement of the stylet handle 130 and the needle hub 110, the removal contact surface 142 of the first beam 132 and the second beam 134 cam against the corresponding second portion 124 of the first member 116 and the second member 118 to release the stylet handle 130 from the needle hub 110.

Referring to FIGS. 13-18, in yet another embodiment of the present invention, an alternative stylet handle 310 is shown. As shown in FIGS. 13-18, the protrusion 316 includes a first beam 318 and a second beam 320, with each beam having a restraining end 322. The protrusion 316 is positioned within a face of the housing 324 such that the protrusion 316 is aligned on one side of the stylet receiving port 326 adapted to receive the stylet (not shown) therein. Optionally, the stylet handle 310 may include a mating ring 328 for engaging the open end 36 of the transparent portion 35, shown in FIG. 9, to form a fluid impervious seal therewith.

While several embodiments of the invention were described in the foregoing detailed description, those skilled in the art may make modifications and alterations to these embodiments without departing from the scope and spirit of the invention. Accordingly, the foregoing description is intended to be illustrative rather than restrictive.

What is claimed is:

1. A hub assembly, comprising:
   a needle hub having a proximal end and a distal end, having a cannula extending therethrough and protruding from the distal end, the needle hub having a first engagement portion; and
   a stylet handle having a stylet extending therefrom, the stylet adapted to be received within a portion of the cannula, the stylet handle having a second engagement portion;
   wherein an engagement of the first engagement portion of the needle hub and the second engagement portion of the stylet handle forms a positive lock, which restricts the first engagement portion from separating from the second engagement portion in a longitudinal direction,
   wherein the first engagement portion is a recess and the second engagement portion is a protrusion for releasable receipt within the recess,
   wherein the protrusion comprises a first beam and a second beam spaced apart from the first beam, the second beam extending along and substantially parallel to the first beam,
   wherein the first beam comprises an insertion contact surface adjacent a distal end of the stylet handle and a removal contact surface proximally spaced from the insertion contact surface, and the second beam comprises an insertion contact surface adjacent the distal end of the stylet handle and a removal contact surface proximally spaced from the insertion contact surface of the second beam, the removal contact surface of the first beam and the removal contact surface of the second beam being inclined relative to a longitudinal axis of the protrusion,
   wherein the recess further comprises a shoulder and the protrusion further comprises a restraining end engageable with the shoulder when the needle hub and the stylet handle form the positive lock, and
   wherein the recess comprises a first portion for engaging the insertion contact surface of the first beam and the insertion contact surface of the second beam during transition of the protrusion from an unlocked position to the positive lock, and a second portion for engaging the removal contact surface of the first beam and the removal contact surface of the second beam during transition of the protrusion from the positive lock to the unlocked position.

2. The hub assembly of claim 1, wherein the insertion contact surface of the first beam and the insertion contact surface of the second beam extends from at least one of laterally or radially from the longitudinal axis of the protrusion and is are inclined in a direction from a distal end of the restraining end to a proximal end of the restraining end, and wherein the removal contact surface of the first beam and the removal contact surface of the second beam extend from at least one of laterally or radially from the longitudinal axis of the protrusion and are inclined in a direction from the proximal end of the restraining end to the distal end of the restraining end.

3. The hub assembly of claim 1, wherein at least one of the first beam and the second beam is adapted to transition from one of the unlocked position and the positive lock to the other of the unlocked position and the positive lock.

4. The hub assembly of claim 1, wherein the first beam and the second beam are deflected toward each other during transition of the protrusion from one of the unlocked position and the positive lock to the other of the unlocked position and the positive lock.

5. The hub assembly of claim 4, wherein each of the first beam and the second beam is adapted to deflect from about 0.005 inches to about 0.010 inches during transition from one of the unlocked position and the positive lock to the other of the unlocked position and the positive lock.

6. The hub assembly of claim 1, wherein the insertion contact surface of the first beam and the insertion contact surface of the second beam extend laterally from the longitudinal axis of the protrusion and are inclined in opposing directions from a distal end of the restraining end to a proximal end of the restraining end.

7. The hub assembly of claim 1, wherein the removal contact surface of the first beam and the removal contact surface of the second beam extend laterally from the longitudinal axis of the protrusion and are inclined in opposing directions from a proximal end of the restraining end to a distal end of the restraining end.

8. The hub assembly of claim 1, wherein the needle hub and the stylet handle are adapted to transition between one of the unlocked position and the positive lock and the other of the unlocked position and the positive lock, and wherein the protrusion is in a non-deflected orientation in both the unlocked position and the positive lock.

9. The hub assembly of claim 8, wherein the protrusion is deflected against a portion of the recess during transition from one of the unlocked position and the positive lock to the other of the unlocked position and the positive lock.

10. The hub assembly of claim 1, wherein the first engagement portion is oriented on a first side of the needle hub and the second engagement portion is oriented on a first side of the stylet handle, such that the needle hub and the stylet handle may only form the positive lock when the first side of the needle hub and the first side of the stylet handle are aligned adjacent each other.

11. The hub assembly of claim 1, wherein at least one of the engagement or a disengagement of the first engagement portion and the second engagement portion produces an audible, visual or tactual indicator evidencing one of the unlocked position or the positive lock of the needle hub and the stylet handle.

12. The hub assembly of claim 1, wherein the needle hub further comprises a transparent portion to indicate fluid flow through the cannula.

13. The hub assembly of claim 12, wherein the transparent portion has a substantially parabolic curvature.

14. A needle assembly, comprising:
   a cannula having a distal end adapted to penetrate a tissue sample, a proximal end, and a lumen extending between the distal end and the proximal end;

a needle hub connected to the proximal end of the cannula, the needle hub having a first engagement portion;

a stylet having a distal end and a proximal end, the stylet adapted to be received through the lumen; and a stylet handle connected to the proximal end of the stylet, the stylet handle having a second engagement portion;

wherein an engagement of the first engagement portion and the second engagement portion forms a positive lock, which restricts the first engagement portion from separating from the second engagement portion in a longitudinal direction, the positive lock being formed between the needle hub and the stylet handle such that a disengagement force required to release the positive lock is greater than a force applied to the stylet during insertion of the distal end of the cannula in the tissue sample, wherein the first engagement portion is a recess and the second engagement portion is a protrusion for releasable receipt within the recess, wherein the protrusion comprises a first beam and a second beam spaced apart from the first beam, the second beam extending along and substantially parallel to the first beam, wherein the first beam comprises an insertion contact surface adjacent a distal end of the stylet handle and a removal contact surface proximally spaced from the insertion contact surface, and the second beam comprises an insertion contact surface adjacent the distal end of the stylet handle and a removal contact surface proximally spaced from the insertion contact surface of the second beam, the removal contact surface of the first beam and the removal contact surface of the second beam being inclined relative to a longitudinal axis of the protrusion, wherein the recess further comprises a shoulder and the protrusion further comprises a restraining end engageable with the shoulder when the needle hub and the stylet handle form the positive lock, and wherein the recess comprises a first portion for engaging the insertion contact surface of the first beam and the insertion contact surface of the second beam during transition of the protrusion from an unlocked position to the positive lock, and a second portion for engaging the removal contact surface of the first beam and the removal contact surface of the second beam during transition of the protrusion from the positive lock to the unlocked position.

15. The needle assembly of claim 14, wherein the first beam and the second beam are deflected toward each other during transition of the protrusion from one of the unlocked position and the positive lock to the other of the unlocked position and the positive lock.

16. The needle assembly of claim 14, wherein the needle hub and the stylet handle are adapted to transition between one of the unlocked position and the positive lock and the other of the unlocked position and the positive lock, and wherein the protrusion is in a non-deflected orientation in both the unlocked position and the positive lock, and the protrusion is deflected against a portion of the recess during transition from one of the unlocked position and the positive lock to the other of the unlocked position and the positive lock.

17. The needle assembly of claim 14, wherein at least one of the engagement or a disengagement of the first engagement portion and the second engagement portion produces an audible, visual or tactual indicator evidencing one of the unlocked position or the positive lock of the needle hub and the stylet handle.

18. The needle assembly of claim 14, wherein the disengagement force is less than a drag force of the cannula within a human tissue sample.

19. The needle assembly of claim 14, wherein the cannula is an 18 G needle and the disengagement force is at least greater than 0.25 lbs.

20. The needle assembly of claim 14, wherein the disengagement force is less than 0.45 lbs.

21. The needle assembly of claim 14, wherein the cannula is a 22 G needle and the disengagement force is at least greater than 0.09 lbs.

22. The needle assembly of claim 14, wherein the disengagement force is less than 0.27 lbs.

23. The needle assembly of claim 14, further comprising a needle guard circumferentially disposed about a portion of the cannula and at least partially disposable within a portion of the needle hub.

24. A needle assembly, comprising:

a cannula having a beveled distal end adapted to penetrate a tissue sample, a proximal end, and a lumen extending between the distal end and the proximal end;

a needle hub connected to the proximal end of the cannula, the needle hub having a first engagement portion including a first directional indicator corresponding to an orientation of the beveled distal end of the cannula;

a stylet having a beveled distal end and a proximal end, the stylet adapted to be received through the lumen; and a stylet handle connected to the proximal end of the stylet, the stylet handle having a second engagement portion including a second directional indicator corresponding to an orientation of the beveled distal end of the stylet;

wherein an engagement of the first engagement portion and the second engagement portion forms a positive lock, which restricts the first engagement portion from separating from the second engagement portion in a longitudinal direction, and is permitted only when the first directional indicator and the second directional indicator are provided in a mating orientation, wherein the first engagement portion is a recess and the second engagement portion is a protrusion for releasable receipt within the recess, wherein the protrusion comprises a first beam and a second beam spaced apart from the first beam, the second beam extending along and substantially parallel to the first beam, wherein the first beam comprises an insertion contact surface adjacent a distal end of the stylet handle and a removal contact surface proximally spaced from the insertion contact surface, and the second beam comprises an insertion contact surface adjacent the distal end of the stylet handle and a removal contact surface proximally spaced from the insertion contact surface of the second beam, the removal contact surface of the first beam and the removal contact surface of the second beam being inclined relative to a longitudinal axis of the protrusion, wherein the recess further comprises a shoulder and the protrusion further comprises a restraining end engageable with the shoulder when the needle hub and the stylet handle form the positive lock, and wherein the recess comprises a first portion for engaging the insertion contact surface of the first beam and the insertion contact surface of the second beam during transition of the protrusion from an unlocked position to the positive lock, and a second portion for engaging the removal contact surface of the first beam and the removal contact surface of the second beam during transition of the protrusion from the positive lock to the unlocked position.

25. The needle assembly of claim 24, wherein the mating orientation of the first directional indicator and the second directional indicator substantially aligns the beveled distal end of the stylet with the beveled distal end of the cannula.

26. The needle assembly of claim 24, wherein at least one of a formation of the positive lock and a disengagement of the positive lock produces an audible, visual or tactual indicator evidencing one of the unlocked position or the positive lock of the needle hub and the stylet handle.

* * * * *

UNITED STATES PATENT AND TRADEMARK OFFICE
CERTIFICATE OF CORRECTION

| | | |
|---|---|---|
| PATENT NO. | : 9,259,553 B2 | |
| APPLICATION NO. | : 12/275636 | |
| DATED | : February 16, 2016 | |
| INVENTOR(S) | : Peter George Delano et al. | |

It is certified that error appears in the above-identified patent and that said Letters Patent is hereby corrected as shown below:

Claims

Column 14, Line 1, Claim 2, delete "is are" and insert -- are --

Signed and Sealed this
Twenty-fourth Day of May, 2016

Michelle K. Lee
*Director of the United States Patent and Trademark Office*